US009582038B1

(12) United States Patent
Jayaraman et al.

(10) Patent No.: US 9,582,038 B1
(45) Date of Patent: Feb. 28, 2017

(54) SMART HUB FOR SMART GARMENT

(71) Applicant: Sarvint Technologies, Inc., Atlanta, GA (US)

(72) Inventors: Sundaresan Jayaraman, Atlanta, GA (US); Sungmee Park, Atlanta, GA (US)

( * ) Notice: Subject to any disclaimer, the term of this patent is extended or adjusted under 35 U.S.C. 154(b) by 0 days.

(21) Appl. No.: 14/991,422

(22) Filed: Jan. 8, 2016

(51) Int. Cl.
*G06F 1/16* (2006.01)
*G06F 1/18* (2006.01)
*A61B 5/01* (2006.01)
*A61B 5/00* (2006.01)

(52) U.S. Cl.
CPC ............. *G06F 1/1632* (2013.01); *A61B 5/01* (2013.01); *A61B 5/6804* (2013.01); *G06F 1/163* (2013.01); *G06F 1/183* (2013.01)

(58) Field of Classification Search
CPC .............................. G06F 1/163; H05K 5/0047
See application file for complete search history.

(56) References Cited

U.S. PATENT DOCUMENTS

| 4,722,354 A | 2/1988 | Axelgaard |
| 5,374,283 A | 12/1994 | Flick |
| 5,450,845 A | 9/1995 | Axelgaard |
| 6,381,482 B1 | 4/2002 | Jayaraman |
| 6,755,795 B2 | 6/2004 | Marmaropoulos |
| 6,970,731 B1 | 11/2005 | Jayaraman |
| 7,152,470 B2 | 12/2006 | Impio |
| 7,173,437 B2 | 2/2007 | Hervieux |
| 7,970,451 B2 | 6/2011 | Hassonjee |
| 8,082,762 B2 | 12/2011 | Burr |
| 2003/0212319 A1 | 11/2003 | Magill |
| 2004/0263318 A1* | 12/2004 | Dvorak ............. G06F 1/163 340/5.53 |
| 2009/0310290 A1* | 12/2009 | Tennent ............. G06F 1/163 361/679.03 |
| 2015/0145671 A1* | 5/2015 | Cohen ............. G08B 21/18 340/539.11 |
| 2015/0163921 A1* | 6/2015 | Oster ............. H05K 1/181 361/749 |
| 2015/0258458 A1* | 9/2015 | Zhang ............. A63F 13/95 463/40 |
| 2016/0018846 A1* | 1/2016 | Zenoff ............. G09G 3/002 345/174 |
| 2016/0192716 A1* | 7/2016 | Lee ............. A41D 1/002 2/422 |

* cited by examiner

*Primary Examiner* — Anthony Q Edwards

(57) ABSTRACT

Disclosed are various embodiments for a smart hub for a smart garment including a mate-able top housing and a bottom housing, the top housing configured for engagement with a controller, the controller comprising automated computing machinery for information processing functions for the smart garment; an engagement for mating the top housing and the bottom housing; wherein the top housing and the bottom housing form an interior cavity to house a baseboard and a PCB when mated; a baseboard within the interior cavity including a pattern of lead paths conforming at least to a portion of the pinout of the PCB; a plurality of electrical leads within the one or more of the lead paths providing electrical connectivity from a plurality of terminals of the PCB through the baseboard to the controller when installed and providing structural support to maintain the PCB to the baseboard.

17 Claims, 8 Drawing Sheets

SMART HUB FOR SMART GARMENT

BACKGROUND

Wearable computers, also known as body computers or wearables, are often implemented as miniature electronic devices that are worn by a user and provide computer functionality in response to one or more user conditions. Such wearable technology has been developed for general or special purpose information technologies and media development. Wearable computers are especially useful for applications that require more complex computational support than just hardware coded logics. Examples of wearable computers include smart watches, smart eyeglasses, and many others.

Another example of such wearable technology is wearable smart garments. Smart garments are often made with sensors, actuators, information processing components and other components that provide some form of interaction with a user wearing the garment, or some form of data, information processing, or data communications.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Figure 1:
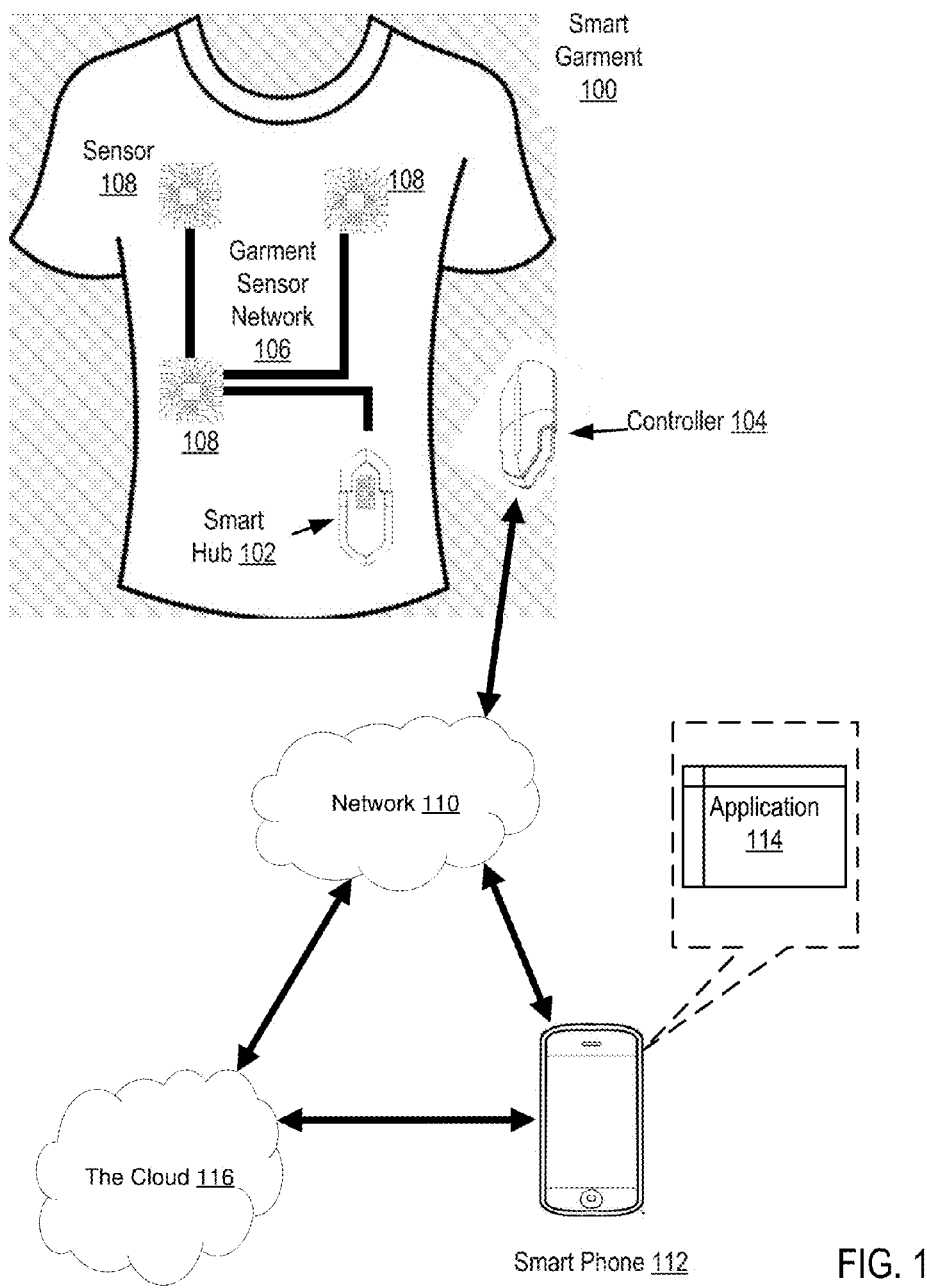
FIG. 1 sets forth a system diagram illustrating aspects of smart hubs and smart garments according to embodiments of the present invention.

Wearable smart hubs and smart garments according to embodiments of the present invention are described with reference to the accompanying drawings, beginning with FIG. 1. FIG. 1 sets forth a system diagram illustrating aspects of smart hubs and smart garments according to embodiments of the present invention. The smart garment of FIG. 1 is a form of wearable article that provides functionality for sensing various user or environmental conditions, functionality for information processing based upon user or environmental conditions or other sensing, information processing, data processing, or computational functions as will occur to those of skill in the art. Smart garments according to various embodiments of the present invention are often implemented as shirts, socks, hats, pants, bras, sports clothing, underwear, shoes, watchbands, belts, personal items, accessories, and other smart garments as will occur to those of skill in the art.

The smart garment (100) of FIG. 1 is illustrated as a smart shirt. This is for example and not for limitation. As mentioned above, smart garments according to embodiments of the present invention are articles that come in many forms.

In the example of FIG. 1, the smart garment (100) has installed upon it a smart hub (102). Smart hubs according to embodiments of the present invention typically provide a consistent and reliable interface in the form of a docking station or attachment mechanism for the controller such that the controller may perform its intended functions when that controller is engaged with the smart hub. Smart hubs according to typical embodiments of the present invention provide an interface from a controller installed within it for bi-directional signal or data communications with one or more sensors, components, or information processing functionality provided by the smart garment.

The smart garment of FIG. 1 includes a number of sensors (108) installed upon it and coupled for data communications with the smart hub (102) through a smart garment network (106). Sensors useful in smart garments according to embodiments of the present invention may include fabric based sensors such as those described in U.S. Pat. Nos. 6,145,551; 6,381,482; and 6,970,731, all of which are incorporated herein by reference in their entirety. Other sensors useful with smart garments according to embodiments of the present invention include electrodes positioned to contact the wearer of the smart garment, electrical sensors for measuring electrical impulses of the wearer, and any other sensor that will occur to those of skill in the art. Such sensors may be used to derive information describing the current state of the wearer, the current environmental state surrounding the smart garment, use of the smart garment, historical information describing the user and environmental conditions and many others as will occur to those of skill in the art. More particularly, sensors according to embodiments of the present invention are often used for heart monitoring, respiration monitoring, monitoring the condition of the smart garment itself, measuring EKG, measuring EEG, measuring EMG, measuring body temperature, determining ambient temperature, measuring galvanic skin response, and measuring many other biometric or environmental conditions as will occur to those of skill in the art.

The plurality of sensors (108) of the smart garment (100) of FIG. 1 are coupled for data communications with a smart hub (102) through a garment sensor network (106). That is, the components of the smart garment are coupled for data communications such as signal, data, or electrical communications.

Data communications according to embodiments of the present invention may be wired or wireless. The smart garment network (106) in the example of FIG. 1 is depicted as a wired network. That is, the smart garment of FIG. 1 is illustrated as having conductive paths for data communications from the sensors (108) to the smart hub (108). Wired networks may be implemented as one or more conductive paths from at least one the sensors of the smart garment to the smart hub implemented through conductive fibers woven or knitted into the smart garment, conductive paths pasted upon the smart garment, conductive paths chemically implanted upon the smart garment, conductive paths stitched onto the smart garment, or any other conductive path physically connecting the sensor (108) and the smart hub (102) that is constructed into or onto the smart garment itself as will occur to those of skill in the art.

Smart garment networks according to embodiments of the present invention may also be wireless. In such wireless smart garment networks, the sensors (108) may be coupled for data communications with a smart hub (102) and other components of a smart garment and peripherals through a wireless network implemented in any number of wireless protocols and standards such as Cellular Networks—Wide Area Networks ('WAN'), Local Area Networks ('LAN'), Wireless Sensor Networks ('WSN'), Personal Area Networks ('PAN'), utilizing standards such as BLUETOOTH™, ANT, WI-FI, LI-FI, 2G, 3G, 4G, LTE or any suitable protocol or wireless standard that will occur to those of skill in the art. Often in wireless embodiments, the sensors themselves may be connected to some form of wireless adapter capable of transmitting or receiving information wirelessly to or from the smart hub (102), networked peripheral device, or any other peripheral such as wireless adapter serving a network or set of networks.

As mentioned above, the smart hub (102) of FIG. 1 is installed upon a smart garment (100) and provides an interface for signal and data communications between sensors and other components of the smart garment (100) and a controller (104). The controller (104) of FIG. 1 is a form of automated computing machinery which provides functionality to the smart garment either in the form of functionality provided as a result of values received from the sensors or information processing functions of the smart garment, through bi-directional communications with components of the smart garment or any other functionality that will occur to those of skill in the art. The controller of FIG. 1 provides bi-directional access and functionality with either onboard functionality on the controller itself or through data communications through the controller with one or more additional peripherals.

In the example of FIG. 1, the smart garment (100) and its components are coupled for data communications with a number of peripherals (110, 116, and 112) through the garment sensor network (106), the smart hub (102), and the controller (104). Peripherals according to embodiments of the present invention include devices in data communications with or operating to provide functionality with the smart garment and its components either though wired or wireless communications. Examples of peripherals include physical devices, logical devices, hardware devices, software functions or applications, or any other device external to the smart hub or controller that interacts with or provides or engages in data communications or functionality to the smart garment as will occur to those of skill in the art. Such peripherals include, for example, smart phones, smart watches, smart eyeglasses, helmets, hats, tablets, laptops, desktops, the cloud, networked devices, peer-to-peer networked devices, local area networks, wide area networks, the cloud, or any other peripheral that will occur to those of skill in the art.

In the example of FIG. 1, the smart garment (100) is coupled for data communications to a smart phone (112) through a network (110). The network (100) of FIG. 1 may be implemented as a local area network ('LAN'), wide area network ('WAN'), Wireless Sensor Network ('WSN'), Personal Area Network ('PAN'), a peer-to-peer network, or any other form of network as will occur to those of skill in the art. The smart phone is provided for explanation and not for limitation. In fact, any number of peripherals may be useful with smart hubs and smart garments according to embodiments of the present invention.

The smart phone (112) has installed upon it an application (114). The application (114) of FIG. 1 is an example of software executing on the smart phone (114) that provides wearable computing functions useful to a user when used with the smart garment, in this case, a smart shirt. The application of FIG. 1 may provide functionality such as storing, monitoring, reporting, manipulating, presenting, or otherwise using data or signals received from the sensors (108) or other components of the smart garment (100). The application of FIG. 1 may be implemented as an application for health management and administration, safety management and administration, or any other applicable use with the smart garment as will occur to those of skill in the art.

In the example of FIG. 1, the smart garment (100) is coupled for data communications through the smart hub (102), the controller (104), and the network (110) to the cloud (116). The cloud (116) of FIG. 1 is a representation of distributed computing resources as will occur to those of skill in the art. The cloud enables resources to be provided to and received from the smart garment, the smart hub, and the controller as will occur to those of skill in the art. The cloud also enables such resources to be provided to and received from the smart phone of FIG. 1 for additional use with the smart garment (100). The use of the cloud in the example of FIG. 1 is for explanation and not for limitation. In fact, many additional distributed resources may be useful to smart hubs and smart garments according to the present invention and all such distributed and networked resources are within the scope of the present disclosure as will occur to those of skill in the art.

The smart hub (102) of FIG. 1 advantageously provides an interface between a controller (104) and various sensors (108) and other components of the smart garment (100) and the garment sensor network. The smart hub (102) of FIG. 1 is adapted to receive a removable controller (104) and provide bi-directional communications to and from the controller (104) and provide those bi-directional communications through the smart garment network (106) to the sensors (108) and other components of the smart garment (100)

In typical embodiments of the present invention, the smart hub (102) of the smart garment has a water-resistant housing containing a printed circuit board ('PCB') designed for use and interaction with the sensors (108) and other components of the smart garment (100) through the smart garment network, as discussed in more detail below. The smart hub of FIG. 1 has a water-resistant housing such that the smart garment (100) may be repeatedly washed without damaging the PCB and other components residing within the smart hub. The smart hub (102) of FIG. 1 is fashioned for physical engagement with the controller (104) such that when the controller is physically engaged with the smart hub, the controller provides bi-directional communications with the sensors and other components of the smart garment. In such embodiments, the controller may be usefully engaged with the smart hub while the user is wearing and using the smart garment and may be usefully disengaged from the smart hub when the user not using the smart garment, washing the smart garment, charging the controller, or other times of disengagement as will occur to those of skill in the art.

Figure 2:
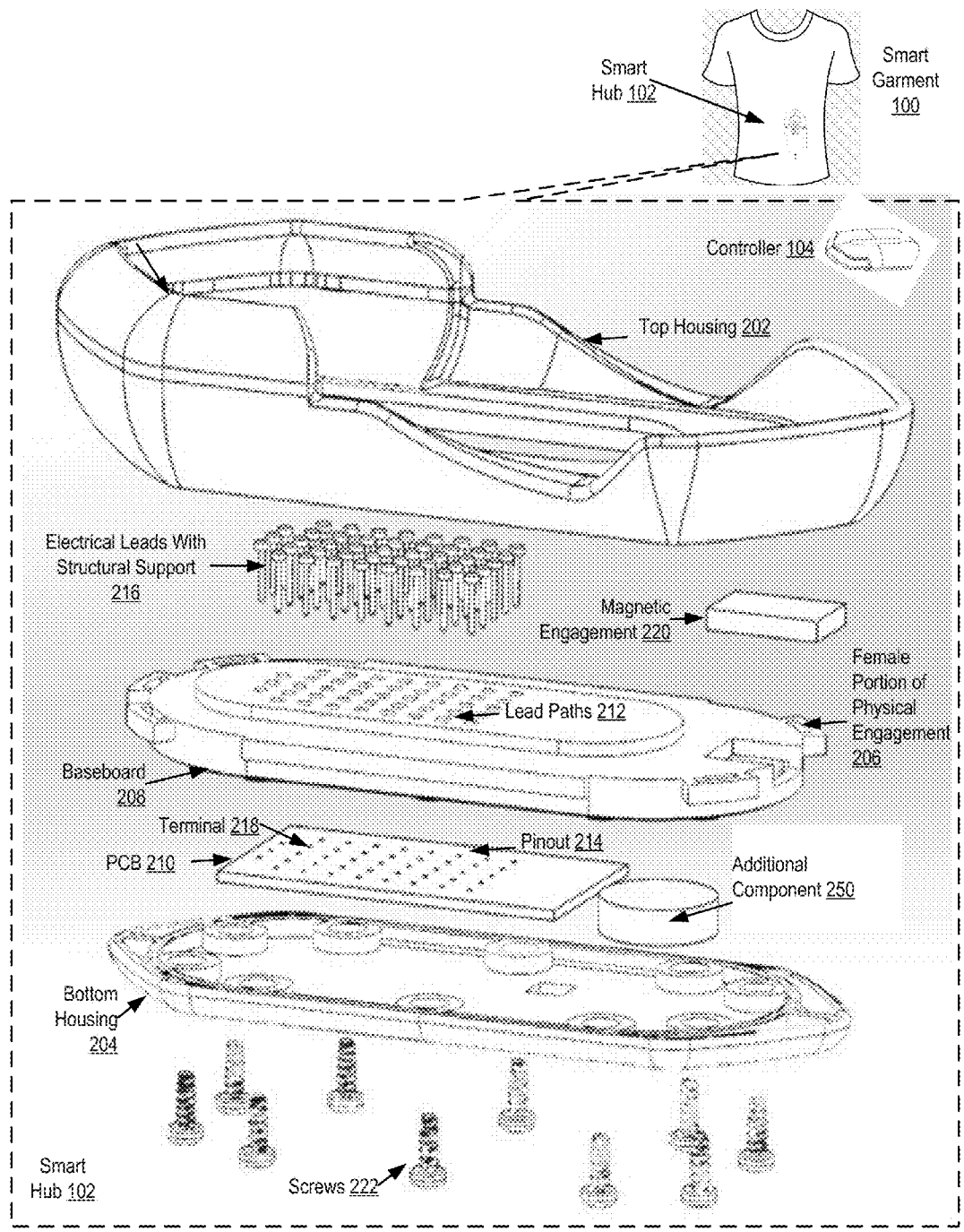
FIG. 2 sets forth a line drawing of an exploded view of an example smart hub for a smart garment according to embodiments of the present invention.

For further explanation, FIG. 2 sets forth a line drawing of an exploded view of an example smart hub (102) for a smart garment (100) according to embodiments of the present invention. The smart hub (102) hub of FIG. 2 includes a mate-able top housing (202) and a bottom housing (204). The top housing and the bottom housing are mate-able in the sense that the smart hub of FIG. 1 provides an engagement to reliably secure the top housing and the bottom housing together. In typical embodiments the top housing (202) and the bottom housing (204) are constructed from thermoplastic materials allowing for the top housing and the bottom housing to be implemented in a number of form factors as will occur to those of skill in the art.

The top housing (202) of the smart hub (102) of FIG. 2 is configured for physical engagement with a controller (104). That is, the top housing (202) of the smart hub of FIG. 2 is shaped such that the controller is secured within the smart hub with sufficient stability from physical interaction to make electrical contact with one or more electrical leads of the smart hub as discussed in more detail below.

The smart hub (102) of FIG. 2 also includes an engagement for mating the top housing (202) and the bottom housing (204). Engagements for mating the top housing and the bottom housing according to embodiments of the present invention may be implemented in a number of ways. On example of such an engagement is a male and female engagement designed to physically engage when the top housing (102) and the bottom housing (204) are forced together. Alternatively, the top housing (102) and the bottom housing (204) may be mated through other engagements such as screws, rivets, bolts, clasps, glue or any other engagement that will occur to those of skill in the art. In the example of FIG. 2, the top housing (202) and the bottom housing (204) are mated through a combination of those descried above. The top housing (202) of FIG. 2 is physically mated with a baseboard (208) which in turn is mated with a set of screws (222) with the bottom housing (204).

In the example of FIG. 2, the top housing (202) and the bottom housing (204) form an interior cavity when they are mated to house internal components of the smart hub. In the example of FIG. 2, the interior cavity houses a baseboard (208) and a printed circuit board ('PCB') (210). The baseboard of FIG. 2 is a structural component of the smart hub which provides structure that supports the functionality or stability of one or more components of the smart hub.

The PCB of FIG. 2 mechanically supports and electrically connects various electronic components of the smart hub. PCBs, according to embodiments of the present invention, typically mechanically support and electrically connect electronic components using conductive tracks, pads and other features often etched from copper sheets laminated onto a non-conductive substrate. PCBs can be single sided (one copper layer, for example), double sided (two copper layers, for example) or multi-layer (outer and inner layers). Multi-layer PCB s allow for much higher component density. Conductors on different layers are often connected with plated-through holes called vias. Advanced PCBs may contain components such as capacitors, resistors or active devices embedded in the substrate.

When a board has only copper connections and no embedded components, it may be called a printed wiring board (PWB) or etched wiring board. For the purposes of this disclosure such PWBs and etched wiring boards are referred to as and are considered PCBs. Furthermore, a PCB populated with electronic components is sometimes called a printed circuit assembly (PCA), printed circuit board assembly or PCB assembly (PCBA). Such PCAs and PCBAs are also referred to as and considered PCBs for the purposes of this disclosure.

The baseboard (208) residing within the interior cavity of the smart hub (102) of FIG. 2 includes a pattern of lead paths (212) conforming at least to a portion of the pinout (214) of the PCB (210). A pinout according to embodiments of the present invention provides the form of the contacts, pins, or other electrical connectors of the PCB for electrical connection with a controller (104). When the controller is connected in the example of FIG. 2, electrical contacts of the controller contact electrical leads (216) of the smart hub, which are disposed through the lead paths (212) to the PCB.

In the example of FIG. 2, the plurality of electrical leads (216) disposed within one or more of the lead paths (212) provides at least two functions. The electrical leads (216) provide electrical connectivity from a plurality of terminals (218) of the PCB (210) through the baseboard (208) to the controller (104) when the controller is installed or physically engaged in the smart hub. The electrical leads (216) of FIG. 2 also provide structural support to maintain the PCB (210) to the baseboard (208). As such the electrical leads of FIG. 2 provide both electrical connectivity and structural support to at least some aspects of the smart hub as will occur to those of skill in the art.

In the smart hub of FIG. 2, the lead paths (212) are implemented as guide holes through the baseboard (206) and the electrical leads (216) include pins. Pins are relatively rigid conductive leads on a through-hole component. The term is said to be derived from its physical shape on through-hole components. Such pins may also be referred to as pin headers. In the example of FIG. 2, the electrical leads with structural support (216) are implemented as pins. The pins are in contact with one or more terminals of the PCB through the guide holes of the baseboard. In this example, the pins provide electrical connectivity from terminals on the PCB to the controller when the controller is engaged in the smart hub and also relatively rigid structural support for securing the PCB to the baseboard within the smart hub.

As mentioned above, the smart hub is secured to a smart garment (100). The smart garment (100) includes sensing and information processing components in communication with the PCB (210) of the smart hub (102). The smart hub may be in communication for signal or data communications or any other communications as will occur to those of skill in the art.

While not illustrated in the exploded view of the smart hub (102) of FIG. 2, in typical embodiments, at least a portion of the fabric of the smart garment resides between the top housing and the bottom housing of the smart hub when the smart hub is installed on the smart garment and one or more electrical leads of the smart garment are in electrical communication with the PCB of the smart hub when the smart hub is installed on the smart garment. That is, the bottom housing and the top housing are mated through at least a portion of the fabric of the smart garment. In the example of FIG. 2, additional screws (222) are provided to mate the bottom housing with the baseboard which in turn then is mated through male and female physical engagements (206) with the top housing thereby securing the smart hub to the smart garment.

In the smart hub of FIG. 2, the interior cavity formed by the engagement of the top housing (202) and the bottom housing (204) is water-resistant. Typically, the water resistance is robust enough such that the smart hub may be installed on a smart garment and the smart garment may be repeatedly washed or cleaned without damaging the interior components of the smart hub. Such washing or cleaning may be carried out through routine washing of the garment in a typical washing machine, dry cleaning the garment, or in other ways as will occur to those of skill in the art.

In the example of FIG. 2, to provide water resistance and shock absorption of the smart hub the interior cavity formed by the engagement of the top housing and the bottom housing is potted. Potting according to various embodiments of the present invention may be carried out by filling the assembly of the smart hub with a solid or gelatinous compound for resistance to shock and vibration, and for the exclusion of moisture and corrosive agents. Thermo-setting plastics or silicone rubber gels are often used for potting. Silicone or epoxy is often used to protect from impact and loose wires. Various potting materials may be used with smart hubs according to embodiments of the present invention as will occur to those of skill in the art.

In the smart hub of FIG. 2, the top housing (202) has an aperture (302 on FIG. 4A) exposing at least a portion of the baseboard and the electrical leads through the baseboard. The aperture of FIG. 2 also exposes to the controller a magnetic engagement corresponding with a magnetic engagement of the controller. When the controller of FIG. 2 is engaged with the top housing of the smart hub, the contacts of the controller may mate with the electrical leads of the smart hub and a magnetic engagement provides additional stability and engagement between the smart hub and the controller. The magnetic engagement may be implemented as a magnet or a metal surface to attach to a magnet either of which may be on either the smart hub or the controller.

The smart hub of FIG. 2 also includes an additional component (250). The additional component may be a vibrator, a notification component, read only memory that may include an ID for interrogation by an outside device, or any other component that will occur to those of skill in the art. The placement of a vibrator or other notification sensor advantageously provides a vehicle for communication or notification of the wearer of the smart garment.

The top housing and the bottom housing of smart hubs according to various embodiments of the present invention may be made of thermoplastic material. Thermoplastic material is a plastic material that becomes pliable or moldable above a specific temperature and solidifies upon cooling. Thermoplastic materials may be usefully used to create the form factors useful in smart hubs according to aspects of the present invention.

Figure 3:
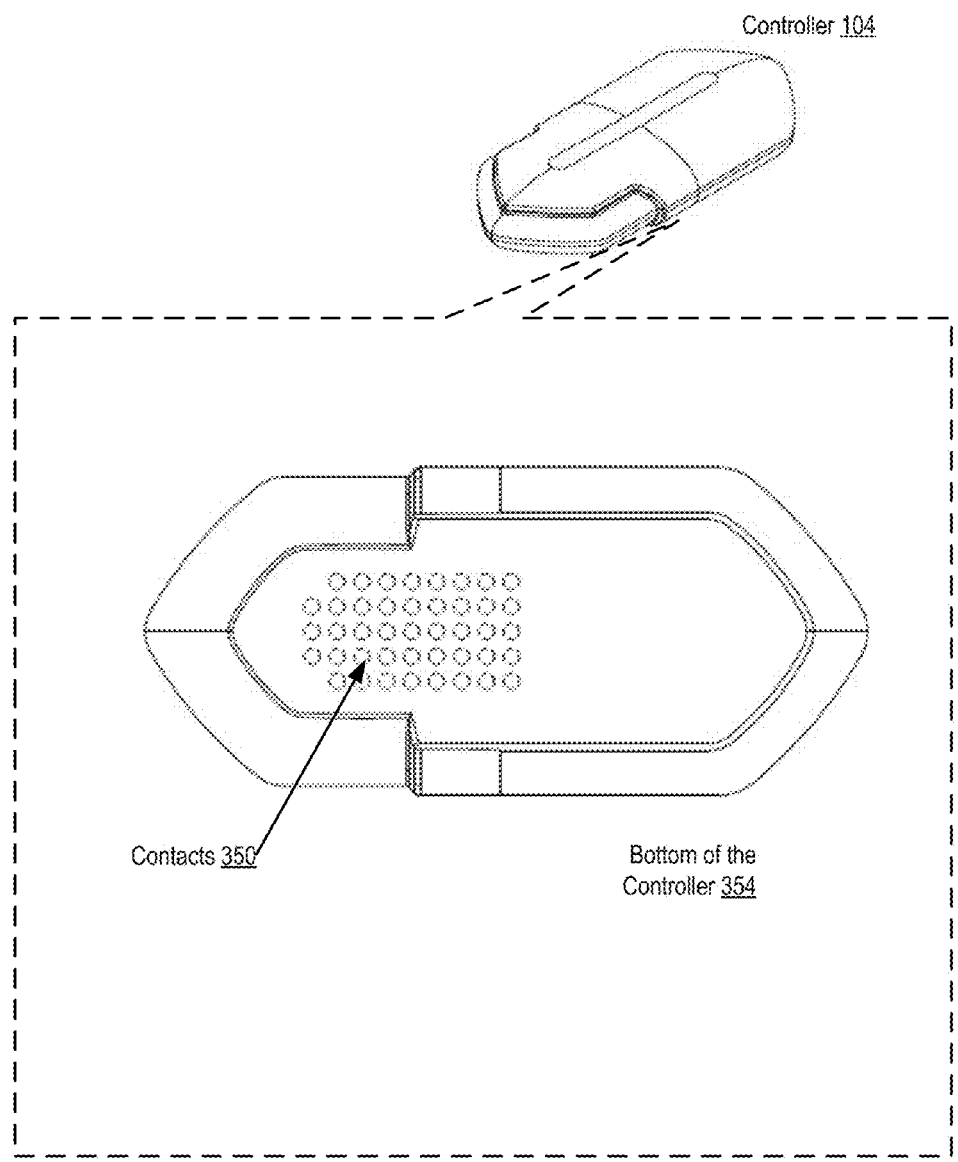
FIG. 3 sets forth a line drawing of a controller useful with smart hubs and smart garments according to embodiments of the present invention.

For further explanation, FIG. 3 sets forth a line drawing of a controller useful with smart hubs and smart garments according to embodiments of the present invention. In the example of FIG. 3, the controller (104) is shown with a callout illustrating the bottom of the controller. The bottom of the controller (354) has a number of contacts (350). The contacts (350) of the controller of FIG. 3 are designed according to the pinout of the PCB of the smart hub of FIG. 2 such that the contacts (350) make contact with the leads of the smart hub when the controller is engaged with the smart hub.

Figure 4A:
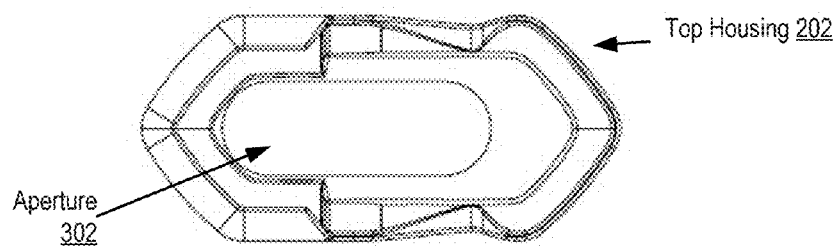
FIG. 4A sets forth a line drawing of an example top housing (202) according to embodiments of the present invention.
Figure 4B:
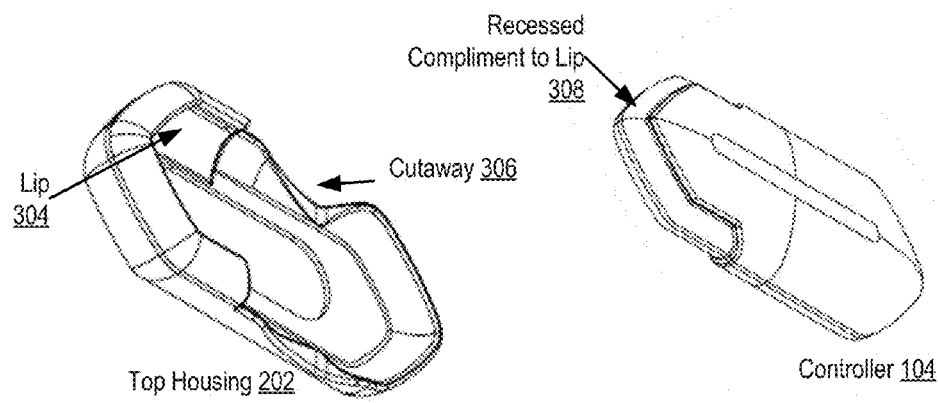
FIG. 4B sets forth a line drawing illustrating aspects of form factors of an example top housing and an example controller according to some embodiments of the present invention.
Figure 4C:
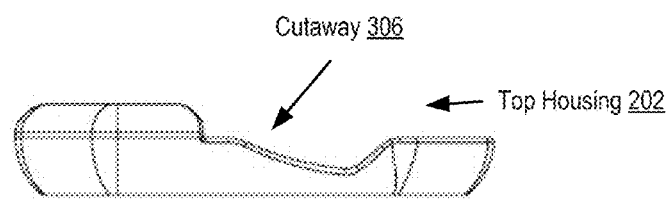
FIG. 4C sets forth a line drawing of side view of the top housing of FIG. 4B.

For further explanation, FIGS. 4A-4C set forth line drawings of example aspects of top housings (202) for smart hubs according to embodiments of the present invention. FIG. 4A sets forth a line drawing of an example top housing (202) according to embodiments of the present invention. The top housing (202) of FIG. 4A has an aperture (302). As mentioned above with reference to FIG. 2, the aperture (302) of FIG. 4A exposes at least a portion of the baseboard and the electrical leads of the smart hub through the baseboard to a controller when the controller is engaged with the smart hub. In this manner the contacts of the controller are secured for communications with the leads of the smart hub such that the controller may provide bi-directional communications and functionality with the smart garment through the smart hub as will occur to those of skill in the art.

The aperture (302) of the top housing in the example of FIG. 4A may in some embodiments also expose a magnetic engagement of the smart hub corresponding with a magnetic engagement of the controller. Such a magnetic engagement may be implemented as a magnet installed on either the controller or the smart hub and a corresponding metallic surface or magnet or magnetic mating surface on either the controller or the smart hub. Such a magnetic engagement provides additional stability and security in the engagement of the smart hub and the controller as will occur to those of skill in the art.

FIG. 4B sets forth a line drawing illustrating aspects of form factors of an example top housing and an example controller according to some embodiments of the present invention. In the example of FIG. 4B, the relative shapes of the top housing (202) and the controller (104) are designed for physical engagement. For further security in that engagement, in the example of FIG. 4B, the top housing (202) has a lip (304) corresponding to a recessed compliment (308) for physical engagement of the top housing and the controller. The lip (304) of the top housing (202) and its complement (308) in the example of FIG. 4B together provide additional security between the controller and the top housing of the smart hub. Such a lip is for explanation and not for limitation. In fact, controllers may be secured within smart hubs in a number of manners such as other relative form factors for physical security, magnetic engagements, clasps, frictional engagements and others as will occur to those of skill in the art.

The example top housing (202) of FIG. 4B also has a cutaway (306) which exposes more of the controller (104) when the controller is installed. This cutaway is to facilitate the removal of the controller from the smart hub by a user. The cutaway of FIG. 4B is for explanation and not for limitation. For further explanation, FIG. 4C sets forth a line drawing of side view of the top housing of FIG. 4B further illustrating the cutaway of FIG. 4B. As will occur to those of skill in the art, such a cutaway advantageously allows a user to easily make contact with the controller while it is engaged in the smart hub and remove it without damage to the smart hub itself. Similarly, the cutaway also advantageously facilitates a user installing the controller within the smart hub.

Smart hubs according to embodiments of the present invention may provide various additional functionality useful administering the smart garments upon which they are installed. One such functionality is the ability to usefully identify the smart hub and by association or directly the smart garment upon which the smart hub is installed. Such functionality is useful in smart closets, inventory tracking, point-of-sale information and many other settings where identifying, tracking, or uniquely administering a smart hub or smart garment is needed or desired.

Figure 5:
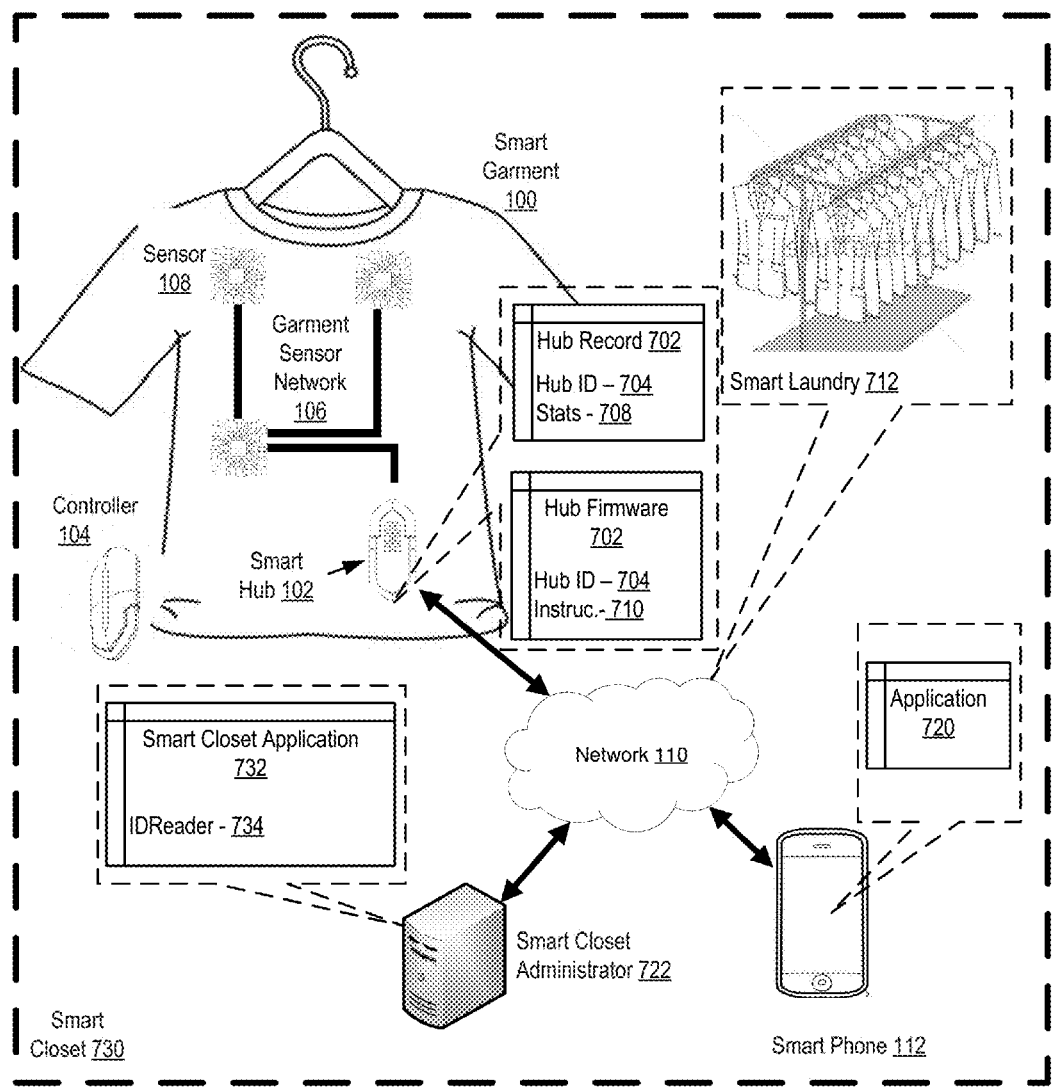
FIG. 5 sets forth a line drawing of a system diagram of a smart hub for a smart garment according to example embodiments of the present invention.

For further explanation, FIG. 5 sets forth a line drawing of a system diagram of a smart hub for a smart garment according to example embodiments of the present invention that includes functionality for identifying the smart hub and either by association or by direct reference identifying the smart garment upon which the smart hub is installed. The smart hub in the example of FIG. 5 is similar to the smart hub of FIG. 2 in that the that smart hub of FIG. 5 includes a housing surrounding and securing a printed circuit board ('PCB') to the smart garment and the PCB is coupled for bi-directional communications with one or more sensors (108) or information processing components of the smart garment (100).

In the example of FIG. 5, the smart hub (102) includes memory storing an identification (704) of the smart hub (102). In the example of FIG. 5, the smart hub (102) has installed upon it in read-only memory ('ROM') firmware containing an identification (704) of the smart hub and computer program instructions (704) for retrieving the identification (704) in response to a request from a device peripheral (732) to the smart hub (102). The identification may be stored in any form such as, for example, an alphanumeric identification or any other identification of the smart hub that will occur to those of skill in the art. The firmware of FIG. 5 provides computer program instructions to receive requests for the identification from a requestor and to respond to the requestor the identification. The smart hub of FIG. 5 may receive such a request and respond with the smart hub identification through wireless or wired data communications according to any number or protocols such as those described above with reference to FIG. 1 as will occur to those of skill in the art.

In the example of FIG. 5, the smart hub (102) is installed upon a smart garment (100) and resides in a smart closet (730). The smart closet (730) of FIG. 5 includes a smart laundry (712) which provides some form of automated or periodic cleaning for the smart garment based upon statistics provide by the smart hub. Often controllers used with smart garments and smart hubs described above are not washable. In typical embodiments of the present invention however, smart hubs are robust and washable. As such, to function in the example of FIG. 5, the smart hub (102) includes some additional functionality that is typically associated with the controller such as an adapter for data communications with the network (110) and volatile memory containing information describing or associated with the smart hub or the smart garment to be communicated with other devices through the network.

In the example of FIG. 5, the smart hub of FIG. 5 includes within it non volatile memory for the storage of information regarding the current state of the smart garment. In the example of FIG. 1, the smart hub maintains one or more hub records (702). The hub record (702) of FIG. 5 is a data structure that includes a hub identification (704) and statistics describing the smart garment upon which the smart hub is installed or describing the smart hub itself. Such statistics may include the date of manufacture of the smart garment, washing instructions for the smart garment, the number of recommended washes for the lifetime of the garment, drying requirements of the smart garment, statistics describing the use or state of the garment such as its age and typical usage derived over time from the sensors and information processing of the smart garment, the location of the garment in the smart closet or any other statistics or data that will occur to those of skill in the art.

In the example of FIG. 5, the smart hub includes a data communications adapter (722 in FIG. 6) for transmitting the identification (704) or other statistics (708) of the smart hub or smart garment from the smart hub to the device peripheral to the smart hub. In the example of FIG. 5, such peripherals include a smart closet administrator (722) implemented as a computer administering the smart closet which is in turn coupled for data communications with a smart phone (112) through the network (110).

The smart closet administrator of FIG. 5 includes a data communications module for a smart closet (730) that provides data communications for a smart closet application (732). The smart closet application (732) of FIG. 5 includes computer program instructions that include an ID reader (734) which is capable of requesting from the smart hub (102) an identification of the smart hub or the smart garment upon which it is installed and one or more statistics regarding the smart garment. In this way, the smart closet application may usefully administer the smart garment within the smart closet to locate the garment, wash the garment, notify a user of the location or wash schedule of the garment, determine the usage of the garment and make suggestions to a user—through for example the application (720) on the smart phone (112) on how to better use the smart garment and administer the smart garment in the smart closet in many other ways as will occur to those of skill in the art.

As mentioned above, smart hubs with data communications capabilities and self-identification capabilities may provide many additional benefits to the smart garment and the user of that smart garment. In some embodiments, the device peripheral to the smart hub includes a data communications module for an inventory application, a point-of-sale application or any other application that usefully provides functionality to individual smart garments as will occur to those of skill in the art.

Figure 6:
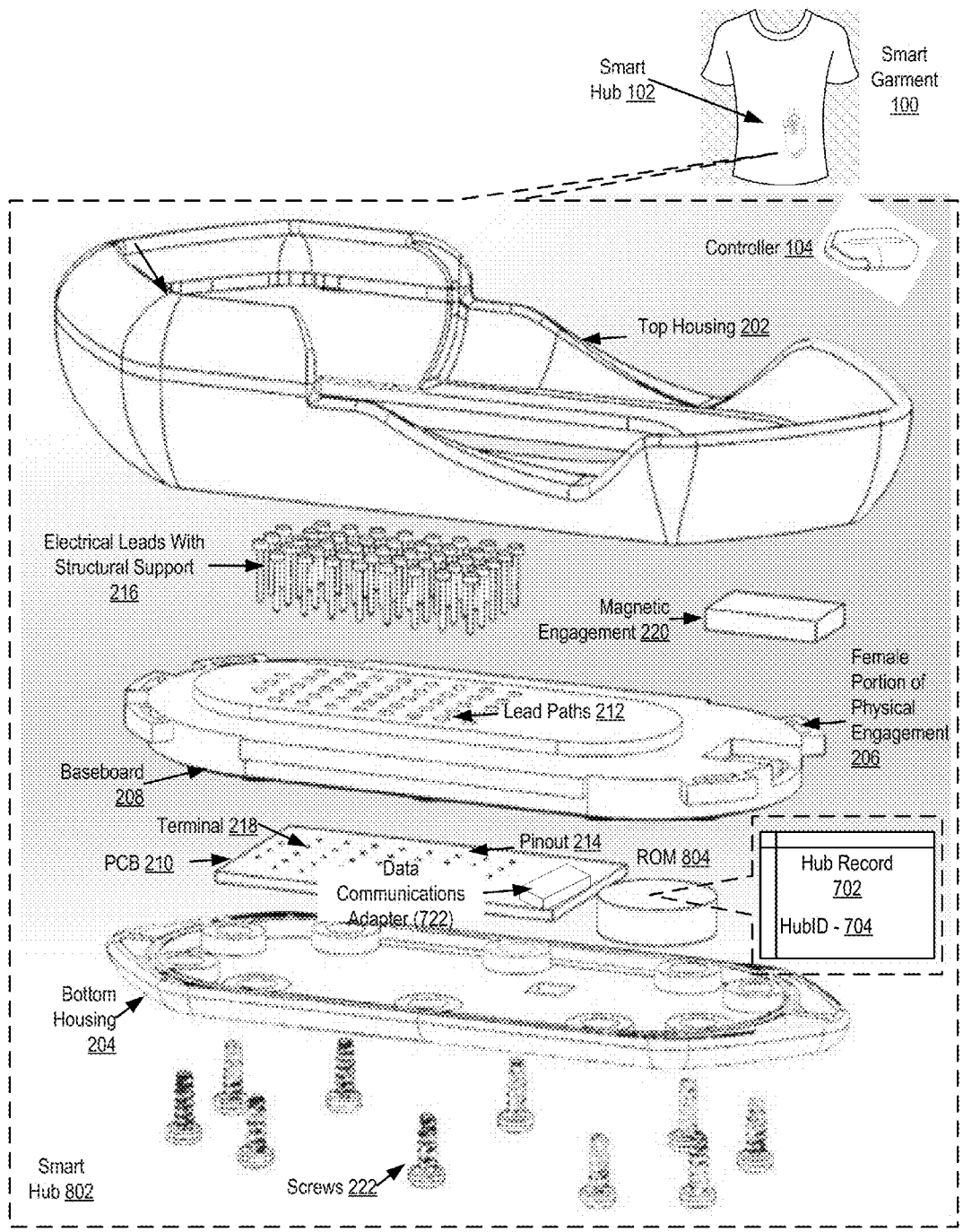
FIG. 6 sets forth an exploded view of the example smart hub of FIG. 5.

For further explanation, FIG. 6 sets forth an exploded view of the example smart hub of FIG. 5. The smart hub (802) of FIG. 6 is similar to the smart hub of FIG. 2 in that the smart hub of FIG. 6 includes a mate-able top housing (202) and a bottom housing (204) and the top housing (202) is configured for engagement with a controller (104). The controller of FIG. 6 is implemented as automated computing machinery capable of bi-directional signal processing, information processing, and other wearable computing functions for the smart garment that will occur to those of skill in the art. In the example of FIG. 6, the top housing and the bottom housing may be made with a thermoplastic material.

The smart hub (802) of FIG. 6 also includes an engagement for mating the top housing (202) and the bottom housing (204) and the top housing and the bottom housing form an interior cavity to house a baseboard (208) and a printed circuit board ('PCB') (210) when mated. The baseboard (208) of FIG. 6 resides within the interior cavity of the smart hub and includes a pattern of lead paths (212) conforming at least to a portion of the pinout (214) of the PCB (210). The baseboard of FIG. 6 also includes a plurality of electrical leads (216) within the one or more of the lead paths (212) providing electrical connectivity from a plurality of terminals (218) of the PCB (210) through the baseboard (208) to the controller (104). The baseboard of FIG. 6 when installed further provides structural support to maintain the PCB (210) to the baseboard (208). The lead paths (212) in FIG. 6 are implemented as guide holes through the baseboard (206) and the electrical leads (216) include a plurality of pins.

In the example of FIG. 6, the controller (104) provides bi-directional signal communications, data communications, and any other data communications between components (108, 106) of the smart garment (100) and a peripheral (112).

In some embodiments of the example of FIG. 6, at least a portion of the fabric of the smart garment resides between top housing and the bottom housing of the smart hub when the smart hub is installed on the smart garment and one or more electrical leads of the smart garment are in electrical communication with the PCB of the smart hub when the smart hub is installed on the smart garment.

In the smart hub of FIG. 6, the interior cavity formed by the engagement of the top housing and the bottom housing is a water-resistant interior cavity that may be potted as described above. Also as described above, in the smart hub (802) of FIG. 6, the top housing (202) has an aperture exposing at least a portion of the baseboard and the electrical leads through the baseboard and an aperture exposing a magnetic engagement corresponding with a magnetic engagement of the controller.

The smart hub of FIG. 6 may also include an additional component or sensor such as a vibrator, a skin conductivity sensor, a haptic feedback component or any other component or sensor that will occur to those of skill in the art.

As described with reference to FIG. 5, the smart hub (802) of FIG. 6 includes a communications adapter (722) which provides data communications to one or more peripherals. The data communications adapter may be implemented as a wireless data communications adapter for wireless communications or an adapter for wired data communications with peripherals and other devices or sensors and other components as will occur to those of skill in the art. The smart hub (802) of FIG. 6 also includes read only memory (804) for storing data and computer program instructions such as firmware to respond to requests for the identification of the smart hub, statistics regarding the smart hub and other information as discussed above with reference to FIG. 6.

In the example of FIG. 6, read only memory (804) also includes a hub record (702) that includes a hub identification (704). The attributes and values of the hub record of FIG. 6 are provided for explanation and not for limitation. In fact, hub records according to embodiments of the present invention may have many additional elements, attributes, and values and such data may be stored in volatile or non-volatile memory as will occur to those of skill in the art.

As mentioned above, smart hubs according to embodiments of the present invention may include a number of additional components such as vibrators, notification devices, and other additional components. One additional component useful in smart hubs according to some embodiments of the present invention include a temperature sensor. For further explanation, FIG. 7 sets forth a line drawing illustrating an exploded view of a smart hub (902) according to example embodiments of the present invention that includes a temperature sensor. The smart hub of FIG. 7 is similar in many aspects to the smart hub of FIG. 6 and the smart hub of FIG. 2 and other example smart hubs described above.

Figure 7:
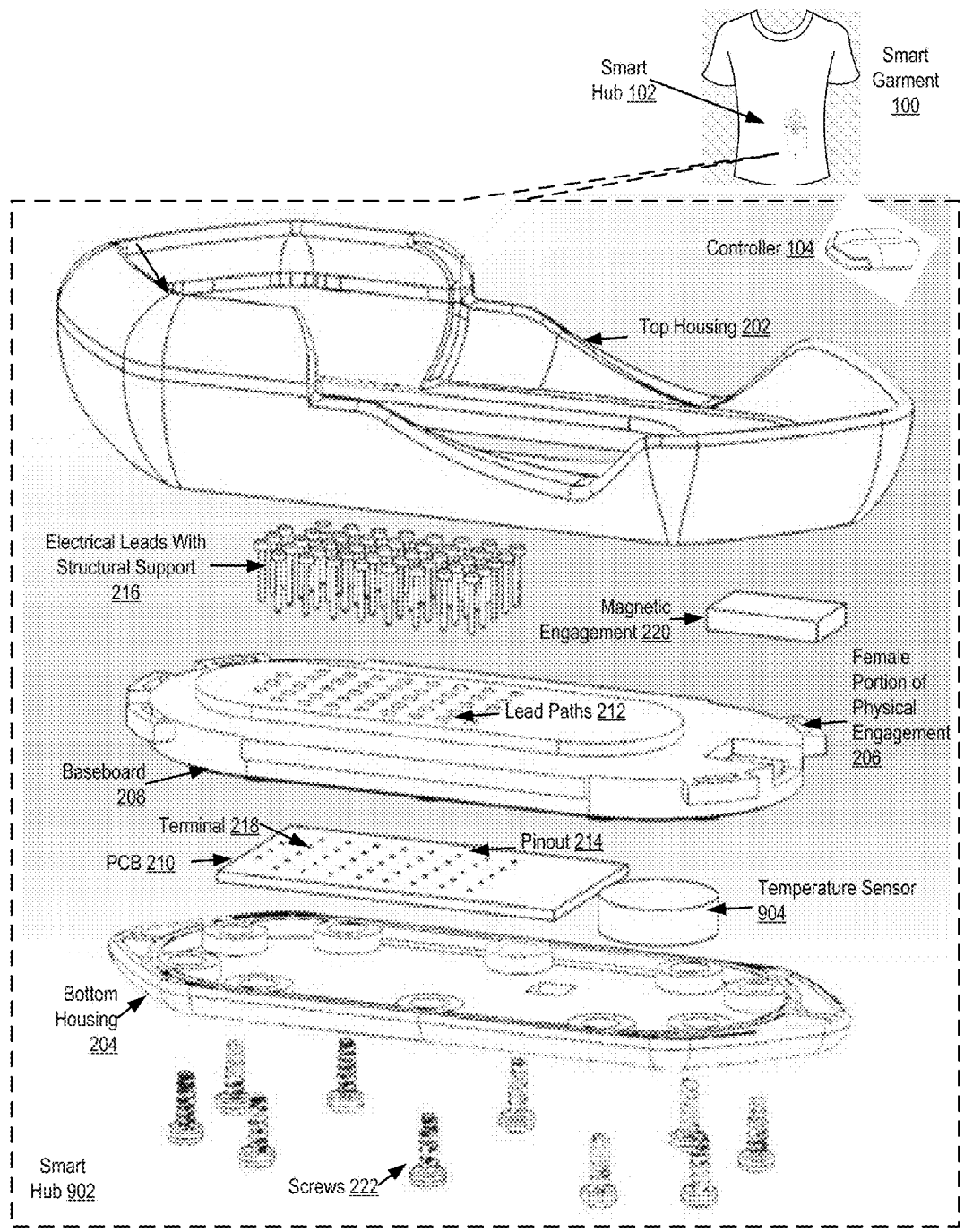
FIG. 7 sets forth a line drawing illustrating an exploded view of a smart hub according to example embodiments of the present invention that includes a temperature sensor.

The smart hub (902) of FIG. 7 is installed on a smart garment (100) and includes a mate-able top housing (202) and a bottom housing (204). The top housing (202) in the example of FIG. 7 is configured for engagement with a controller (104) and that controller is implemented as automated computing machinery providing data communications and information processing functions for the smart garment.

The smart hub (902) of FIG. 7 also includes an engagement for mating the top housing (202) and the bottom housing (204) and the top housing and the bottom housing form an interior cavity to house a baseboard (208). The interior cavity, in the example of FIG. 7, also includes a temperature sensor (902), a printed circuit board ('PCB') (210). The interior cavity of FIG. 7 also has a baseboard (208) with a pattern of lead paths (212) conforming at least to a portion of the pinout (214) of the PCB (210). In the smart hub (902) of FIG. 7, a plurality of electrical leads (216) reside within the one or more lead paths (212) and provide electrical connectivity from a plurality of terminals (218) of the PCB (210) through the baseboard (208) to the controller (104) when installed, and further structural support to maintain the PCB (210) to the baseboard (208).

In the example of FIG. 7, the temperature sensor (904) of the smart hub (902) resides within the housing of the smart hub. As such, in many embodiments the temperature sensor does not itself touch the body of the wearer of the smart garment. However, in such embodiments, the bottom housing often does touch the body of the wearer of the smart garment. Such a bottom housing may be constructed of a thermos-conductive material such that body heat from the wearer is transmitted to the temperature sensor. In such cases, the values read by the temperature sensor may be correlated to a body temperature of the wearer of the smart garment to provide a biometric value for body temperature for use to the wearer. In some embodiments, such temperature readings provide a constant monitoring of the wearer and may be particularly useful for smart hubs implemented in smart garments for exercise and fitness, military applications, health services applications, and many others as will occur to those of skill in the art.

In the example of FIG. 7, the temperature sensor resides within the smart hub. This is for explanation and not for limitation. In alternative embodiments, the temperature sensor may reside outside of the smart hub itself and provide a value to a component within the smart hub.

The smart garment or portions of the smart garment may be made of thermochromic material. Thermochromism is the property of substances to change color due to a change in temperature. The term thermochromic and thermochromatic are often used interchangeably. Thermochromism can appear in thermoplastics, duroplastics, gels or any kind of coatings or in the fibers of the smart garment itself. The fibers of the smart garment may be embedded with a thermochromic additive or a high ordered structure built with a polymer. Thermochromic inks or dyes may also be used to make the smart garment fabric temperature sensitive.

Figure 8:
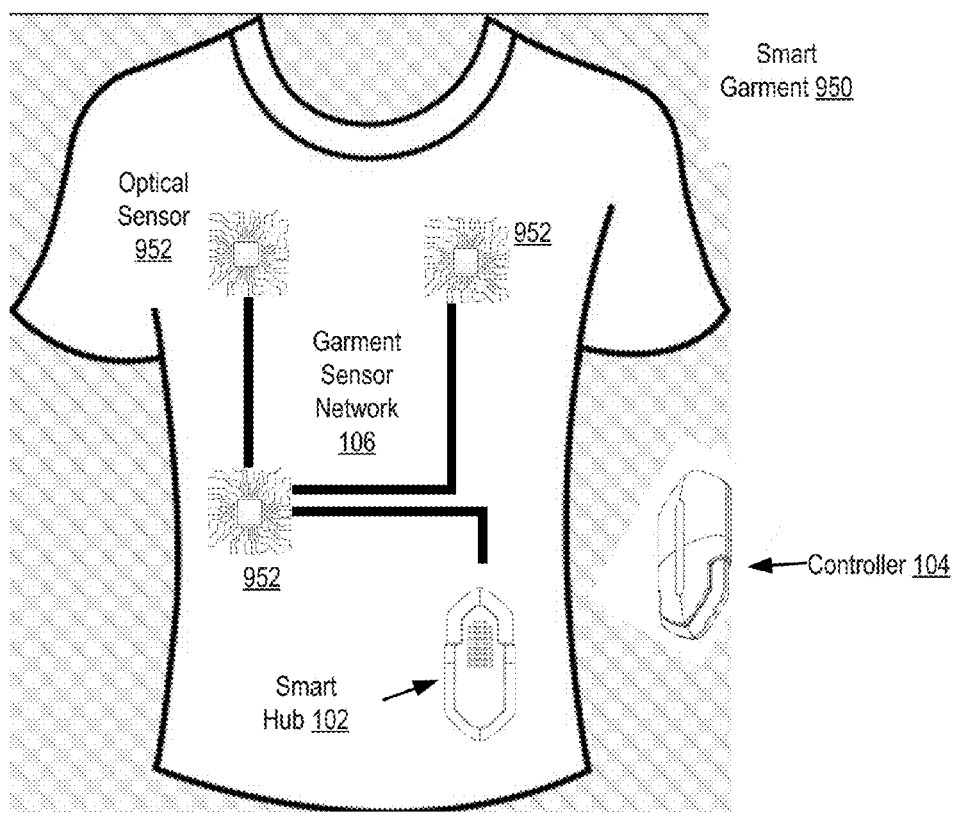
FIG. 8 sets forth a line drawing of a smart garment having some portion of the fabric made of thermocromic material according to example embodiments of the present invention.

For further explanation, FIG. 8 sets forth a line drawing of a smart garment (950) having some portion of the fabric made of thermocromic material according to example embodiments of the present invention. In the example of FIG. 8, the smart garment (950) has a number of optical sensors (952) installed on the smart garment (950) and coupled for data communications through a garment sensor network (106) to a smart hub (102). In the example of FIG. 8, the optical sensors sense and provide a value of the current state of thermochromism of the fabric of the smart garment and transmit that value to the smart hub (102). The values provided by the various optical sensors (952) are received by the smart hub (102) and logic in the smart hub correlates the values to a body temperature value for the user. Such correlation may be carried out through use of data provided by multiple users of smart garments to create correlation formula or table to provide in response to multiple values a single value for body temperature.

In alternative embodiments, values provided from optical sensors may be correlated to ambient or environmental temperature. In such embodiments, optical sensors may be installed on the smart garment in a manner that is on a location of the smart garment that is designed to best represent the ambient or environmental temperature surrounding the smart garment.

It should be emphasized that the above-described embodiments of the present disclosure are merely possible examples of implementations set forth for understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A smart hub for a smart garment, the smart hub comprising:
a mate-able top housing and a bottom housing,
the top housing configured for engagement with a controller, the controller comprising automated computing machinery for information processing functions for the smart garment;
an engagement for mating the top housing and the bottom housing;
wherein the top housing and the bottom housing form an interior cavity to house a baseboard, a temperature sensor, and a printed circuit board ('PCB') when mated;
a baseboard within the interior cavity including a pattern of lead paths conforming at least to a portion of the pinout of the PCB;
a plurality of electrical leads within the one or more of the lead paths providing electrical connectivity from a plurality of terminals of the PCB through the baseboard to the controller when installed and providing structural support to maintain the PCB to the baseboard.

2. The smart hub of claim 1 further comprising logic correlating the output of the temperature sensor with the body temperature of a wearer of the smart garment.

3. The smart hub of claim 1 further comprising logic correlating the output of the temperature sensor with the temperature of the environment of the smart garment.

4. The smart hub of claim 1 wherein the bottom housing is made of thermoplastic material.

5. The smart hub of claim 1 wherein the top housing is made of thermoplastic material.

6. The smart hub of claim 1 wherein the smart garment includes at least a portion of thermochromic material and the smart hub receives from an optical sensor one or more values associated with the thermochromic material.

7. The smart hub of claim 6 wherein the smart hub includes logic correlating the one or more values associated with the thermochromic material with the body temperature of the wearer of the smart garment.

8. The smart hub of claim 6 wherein the smart hub includes logic correlating the one or move values associated with the thermochromic material with the temperature of the environment of the smart garment.

9. The smart hub of claim 1 wherein the controller provides bi-directional communications between components of the smart garment and a peripheral device.

10. The smart hub of claim 1 wherein the smart garment includes sensing or information processing components in communication with the PCB of the smart hub.

11. The smart hub of claim 10 wherein at least a portion of the fabric of the smart garment resides between top housing and the bottom housing of the smart hub when the smart hub is installed on the smart garment and one or more electrical leads of the smart garment are in electrical communication with the PCB of the smart hub when the smart hub is installed on the smart garment.

12. The smart hub of claim 1 wherein the interior cavity formed by the engagement of the top housing and the bottom housing is a water-resistant interior cavity.

13. The smart hub of claim 1 wherein the interior cavity formed by the engagement of the top housing and the bottom housing is potted.

14. The smart hub of claim 1 wherein the lead paths comprise guide holes through the baseboard and the electrical leads include pin headers.

15. The smart hub of claim 1 wherein the top housing is shaped to receive the controller and to provide frictional engagement to secure the controller.

16. The smart hub of claim 1 wherein the top housing has an aperture exposing at least a portion of the baseboard and the electrical leads through the baseboard.

17. The smart hub of claim 1 wherein the top housing has an aperture exposing a magnetic engagement corresponding with a magnetic engagement of the controller.

* * * * *